(12) United States Patent
Vermeulen et al.

(10) Patent No.: US 10,433,738 B2
(45) Date of Patent: Oct. 8, 2019

(54) METHOD AND APPARATUS FOR OPTICAL SENSING OF TISSUE VARIATION AT INCREASED ACCURACY

(71) Applicant: KONINKLIJKE PHILIPS N.V., Eindhoven (NL)

(72) Inventors: Olaf Thomas Johan Antonie Vermeulen, Eindhoven (NL); Cristian Nicolae Presura, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/347,876

(22) Filed: Nov. 10, 2016

(65) Prior Publication Data

US 2017/0055860 A1 Mar. 2, 2017
US 2017/0325699 A9 Nov. 16, 2017

Related U.S. Application Data

(63) Continuation of application No. PCT/EP2015/060476, filed on May 12, 2015.

(30) Foreign Application Priority Data

May 22, 2014 (EP) .................................. 14169379

(51) Int. Cl.
*A61B 5/00* (2006.01)
*A61B 5/024* (2006.01)

(52) U.S. Cl.
CPC ...... *A61B 5/02427* (2013.01); *A61B 5/02433* (2013.01); *A61B 5/02438* (2013.01);
(Continued)

(58) Field of Classification Search
CPC ............ A61B 5/14552; A61B 5/02416; A61B 5/02433; A61B 5/1455; A61B 5/02007;
(Continued)

(56) References Cited

U.S. PATENT DOCUMENTS 6,997,879 B1 2/2006 Turcott
2002/0173706 A1 11/2002 Takatani
(Continued)

FOREIGN PATENT DOCUMENTS

CN 102499694 A 6/2012
CN 103027690 A 4/2013
(Continued)

OTHER PUBLICATIONS

Kuboyama, "Motion Artifact Cancellation for Wearable Photoplethysmographic Sensor", Submitted to the Dept of Electrical Engineering, Massachusetts Institute of Technology, Jul. 9, 2010, pp. 3-66.

*Primary Examiner* — Mark Remaly

(57) ABSTRACT

The present embodiment relates to a method and apparatus for measuring a tissue variation signal (e.g. a photoplethysmographic (PPG) signal) without large direct current (DC) or low frequency (LF) offset which normally limit the sensor accuracy through motion artefacts and/or dynamic range requirements. The proposed solution is based on a separation of the PPG signal from the disturbance. This can be achieved by creation of a modulated PPG signal, or by creation of a differential PPG signal and an optimized sensor configuration which is adapted to remove DC or LF components.

18 Claims, 6 Drawing Sheets

(52) U.S. Cl.
CPC .......... *A61B 5/7214* (2013.01); *A61B 5/7228* (2013.01); *A61B 5/7225* (2013.01); *A61B 2562/0238* (2013.01); *A61B 2562/04* (2013.01)

(58) Field of Classification Search
CPC .................. A61B 5/02427; A61B 5/0261; A61B 5/0285; A61B 5/029; A61B 5/0295; A61B 5/08; A61B 5/14551; A61B 5/7214; A61B 5/7228; A61B 5/7235; A61B 5/7239
See application file for complete search history.

(56) References Cited

U.S. PATENT DOCUMENTS

| | | |
|---|---|---|
| 2003/0036685 A1 | 2/2003 | Goodman |
| 2003/0117698 A1* | 6/2003 | Williams ............ H03G 3/3084 359/341.41 |
| 2008/0306366 A1 | 12/2008 | Ohki et al. |
| 2009/0306487 A1 | 12/2009 | Crowe et al. |
| 2011/0066381 A1 | 3/2011 | Garudadri et al. |
| 2012/0218541 A1* | 8/2012 | Barrett ............... A61B 5/14557 356/39 |
| 2013/0261415 A1 | 10/2013 | Ashe et al. |
| 2015/0257708 A1* | 9/2015 | Winokur ............. H03K 5/1252 600/479 |

FOREIGN PATENT DOCUMENTS

| | | |
|---|---|---|
| EP | 1475035 B1 | 6/2011 |
| JP | 2000325330 A | 11/2000 |
| JP | 2002303576 A | 10/2002 |
| JP | 2005052385 A | 3/2005 |
| JP | 2006098881 A | 4/2006 |
| JP | 2008532680 A | 8/2008 |
| JP | 2010521266 A | 6/2010 |
| JP | 2011206286 A | 10/2011 |
| JP | 2013515528 A | 5/2013 |
| WO | 1999032030 A1 | 7/1999 |
| WO | 2007012931 A2 | 2/2007 |
| WO | 2008116835 A1 | 10/2008 |
| WO | 2008154643 A1 | 12/2008 |
| WO | 2011076886 A2 | 6/2011 |
| WO | 2012108895 A1 | 8/2012 |
| WO | 2012134395 A1 | 10/2012 |
| WO | 2013095861 A1 | 6/2013 |
| WO | 2013181368 A1 | 12/2013 |
| WO | WO 2015176999 A1 * | 11/2015 ........... A61B 5/7214 |

\* cited by examiner

METHOD AND APPARATUS FOR OPTICAL SENSING OF TISSUE VARIATION AT INCREASED ACCURACY

TECHNICAL FIELD

The embodiment relates to the field of a method and an apparatus for optical sensing of a volumetric variation of tissue, such as—but not limited to—an optical acquisition of a plethysmogram.

BACKGROUND

Photoplethysmography (PPG) is the optical acquisition of a plethysmogram, which is the measurement of a volumetric variation of tissue. PPG often relates to variations of blood volume so that PPG may sometimes be interpreted as PPG of blood volume.

A conventional reflective PPG sensor monitors perfusion of blood to the dermis and subcutaneous tissue of skin through absorption measurement at a specific wavelength. Besides light originating from blood there is a far greater portion detected originating from tissue and or blood slushing.

FIG. 1 shows two typical conventional PPG implementation forms. The left portion of FIG. 1 shows an example of a reflective implementation with an optical transmitter 10 (e.g. light emitting diode (LED), laser diode etc.) and an optical receiver 20 (e.g. photo detector, photo diode, photo transistor etc.). Light emitted by the optical transmitter 10 is reflected at a skin portion of a finger tip 100 of a patient or user and then received as a PPG signal at the optical receiver 20. The right portion of FIG. 1 shows an example of a transitive implementation where light emitted by the optical transmitter 10 is transmitted through a tissue portion of an ear 110 of a patient, and then received as a PPG signal at the photo detector 20 as optical receiver.

PPG signals contain a very small alternating current (AC) signal component (the actual plethysmogram) on top of a very large unwanted offset, usually and incorrectly called the DC (direct current) signal. This DC offset usually comprises a low frequency (LF) component consisting of a large portion of back-scattered light not originating from blood of the patient or user, ambient light (if not filtered), and variations of both caused by e.g. motion. The frequency components of the LF component can include the same frequency as the AC signal to be measured, thereby excluding any frequency domain filtering. A conventional PPG sensor therefore typically measures both signals together and uses signal processing algorithms to separate the different components.

The above components of the PPG signal lead to the problem of a reduced usable dynamic range, since major part of the signal processing resolution (e.g. analog-to-digital converting (ADC) etc.) is wasted on sampling the unwanted DC and LF components.

Moreover, motion introduces large variations in the unwanted DC and LF components, which causes major problems in PPG sensors due to motion artefacts. Therefore, additional motion sensors (e.g. three dimensional (3D) accelerometers, or additional optical sensors) are used for artefact suppression in conventional PPG sensors, which leads to increased complexity of PPG sensor devices.

Conventional proposals to overcome the above problems are mostly based on measuring actual movements and compensate the measured PPG signal (which hopefully includes the same motion artefacts) based on some predetermined correlation algorithm. Mostly, 3D accelerometers have been suggested as suitable motion sensors, but the use of additional pseudo-PPG sensors has also been proposed. These pseudo-PPG sensors use e.g. an infrared (IR) wavelength (where blood is known to have (almost) no absorption), but skin tissue has. These pseudo-PPG sensors thus measure a kind of motion artefact which is used to compensate the unwanted motion artefacts in the actual PPG sensor. The problem with this kind of compensation is that the more the secondary wavelength of the pseudo-PPG signal differs from the primary wavelength of the actual PPG signal, the larger the differences are in the optical parameters of the tissue through which the light propagates. For example, IR light will propagate much deeper into the tissue than the shorter primary wavelength. Therefore, the 'motion' sensed by the secondary wavelength of the pseudo-PPG signal is based on a considerably different volume than that of the primary wavelength of the actual PPG signal. This requires additional compensation, and thus increases complexity.

Furthermore, compensation using 3D sensors has the disadvantage that they are expensive, relatively large and use additional supply current. Again, complex compensation algorithms have to be implemented, which requiring more process power.

Thus, in conventional PPG sensors the unwanted DC and LF components are removed by suitable signal processing after A/D conversion. A conventional PPG sensor therefore typically measures both signals together and uses signal processing algorithms to separate the different components.

As another example of conventional PPG sensors, US2003/036685 discloses a physiological signal monitoring system where two PPG sensors with optical radiation sources are used for providing two different functions. First, they are used as SpO2 sensor, where two separated wavelengths (red and infrared) are used to estimate Hb oxygen saturation (i.e., SpO2). One wavelength (880 nm) were the absorption coefficients are nearly equal, and one (658 nm) where the absorption coefficient differ greatly. Second, they are used as pulse wave velocity sensors based on cross correlation between the two output signals.

SUMMARY

It is an object of the present embodiment to provide an improved approach to measure volumetric variations of tissue, by means of which a larger dynamic range for PPG signals becomes available and additional signal processing algorithms for compensation of unwanted DC and LF components at the receiver side can be prevented.

This object is achieved by an apparatus as claimed in claim 1 and by a method as claimed in claim 15.

Accordingly, one or more optical radiation sources with specific wavelengths located at a steeper portion and thus at substantially different values of an absorption curve of a desired matter (e.g. blood) to be measured, two or more optical radiation detectors and at least one filter are proposed to remove the unwanted DC or LF offset prior to amplification and A/D conversion and thereby reducing the need for signal processing techniques and specific electronics. Less processing leads to cheaper microprocessors and reduced power consumption, thereby reducing complexity and related bill of materials (BOM) and increasing battery life. Moreover, additional sensors are not needed, which further reduces cost, complexity and supply current while at the same time increasing signal fidelity. Because various embodiment removes motion signals, motion artefacts are eliminated (or at least largely attenuated).

According to a first option, a modulator may be provided for modulating the amplitudes of the first and second optical signals out of phase at a predetermined frequency, wherein the at least one filter comprises a capacitor or a DC restoration loop for removing a DC component as the unwanted component of the first and second portions. Thus, unwanted DC and LF components can be removed by simply switching the first and second optical signals on and off and filtering the AC component of the detector output signal. More specifically, the unwanted offset signal will also be modulated, but its modulation amplitude will be significantly smaller or reduced (because of the slope differences).

According to a second option which can be combined with the first option, the first and second wavelengths may be selected from an amber or blue wavelength region.

According to a third option which can be combined with the first or second option, a further modulator may be provided for modulating the amplitudes of the first and second optical signals by a further predetermined frequency which differs from the predetermined frequency, to thereby introduce an unbalance of intensities of the first and second optical signals so as to obtain a motion component in the first and second portions. This provides the advantage that the proposed sensing apparatus may also be used as a motion detector.

According to a fourth option which can be combined with any of the first to third options, the at least one filter may comprises a first band-pass filter for filtering the first wavelength and for supplying the filtered output signal to a first optical radiation detector of the at least one optical radiation detector, and a second band-pass filter for filtering the second wavelength and for supplying the filtered output signal to a second optical radiation detector of the at least one optical radiation detector, wherein the apparatus may be adapted to subtract electrical output signals generated by the first and second optical radiation detectors from each other to suppress the unwanted component. Due to the fact, that the first and second electrical output signals are subtracted, unwanted DC components can be suppressed and the desired AC component generated by the specific absorption characteristic of the matter to be measured (e.g. blood) can be extracted at a very early processing stage prior to amplification and subsequent signal processing.

According to a fifth option which can be combined with any of the first to fourth options, the at least one optical radiation source may comprise a first optical radiation source for generating the first optical signal and a second optical radiation source for generating the second optical signal, wherein the apparatus may further comprise a feedback loop for controlling the first and second optical radiation sources in response to a detected remaining amount of the unwanted component. Thereby, any unbalance between the first and second optical signals can be automatically corrected by the feedback loop which acts as a DC cancelation loop for canceling any remaining unwanted DC components at the sensor output.

According to a sixth option which can be combined with any of the first to fifth options, a controllable current divider may be provided for adjusting the ratio of the electrical output signals of the first and second optical radiation detectors based on a control signal generated by a feedback loop in response to a detected remaining amount of the unwanted component. Thereby, an alternative DC cancelation loop can be provided, which is adapted to adjust the ratio of the detector currents based on a remaining DC component in the sensor output signal.

According to a seventh option which can be combined with any of the first to sixth options, a switched integrator amplifier may be provided for amplifying the resultant signal of the subtracted electrical output signals. Thereby, a large amplification with superior signal-to-noise ratio can be obtained. In a specific example of the seventh option, the switched integrator amplifier may be provided in a current-to-time converter circuit. Thereby, the conventional ADC is no longer necessary.

According to an eighth option which can be combined with any of the first to seventh options, the at least one optical radiation source may be adapted to generate a third optical signal of a third wavelength, wherein the first, second and third optical wavelengths are selected so that the value of the wavelength-dependent absorption coefficients of the other matter at the second wavelength equals the average of the values of the wavelength-dependent absorption coefficients of the other matter at the first and third wavelengths, wherein the at least one filter comprises a first filter for filtering the second wavelength only and for supplying the filtered output signal to a first optical radiation detector of the at least one optical radiation detector and a second filter for filtering the first and third wavelengths only and for supplying the filtered output signal to a second optical radiation detector of the at least one optical radiation detector, and wherein the apparatus is adapted to subtract electrical output signals generated by the first and second optical radiation detectors from each other to suppress the unwanted component. This eighth option provides a further alternative solution for early suppression of unwanted DC or LF components prior to amplification and subsequent signal processing. By suitably selecting the wavelengths of the three optical signals, the unwanted components can be suppressed by simply subtracting electrical output signals of the detectors.

In a specific example of the eighth option, the first and second optical radiation detectors (D1, D2) may be scaled by size and or sensitivity. This measure ensures that the unwanted components are reliably suppressed.

It is noted that the above apparatus may be implemented based on discrete hardware circuitries with discrete hardware components, integrated chips, or arrangements of chip modules, or based on signal processing devices or chips controlled by software routines or programs.

It shall be understood that the apparatus of claim 1 and the method of claim 15 may have similar and/or identical embodiments, in particular, as defined in the dependent claims.

It shall be understood that various embodiments can also be any combination of the dependent claims or above embodiments with the respective independent claim.

These and other aspects will be apparent from and elucidated with reference to the embodiments described hereinafter.

DETAILED DESCRIPTION OF EMBODIMENTS

Various embodiment are now described based on a PPG sensor device with small and efficient sensing front-end for heart rate monitoring.

According to a first embodiment, interference caused by unwanted frequency components in the measurand are alleviated by use of modulation. The introduced modulation will transfer the measurand and interference with different efficiencies to a different frequency region and thus will allow measuring the measurand with reduced interference through synchronous detection. It is noted that the above modulation will of course also effect the interference, e.g., melanin absorption will also be modulated. However, because of the large slope differences the amplitude of the interference in the modulated signal will be much lower than that of the measurand.

In the case of a PPG sensor device, the measurand corresponds to the absorption of the emitted light by blood volume, and modulation of this signal can be achieved through the use of two (or more) alternating wavelengths, each with different absorption values for blood. As mentioned above, using different wavelengths has the disadvantage that motion artefacts are picked up because absorption and scattering parameters of tissue through which the light propagates to and from the blood vessels are also wavelength-dependent. Therefore, the chosen wavelengths should be the same or at least similar for motion artefacts, while still having different absorption coefficients for blood. A close approximation is achieved in a specific small wavelength region.

Figure 1:
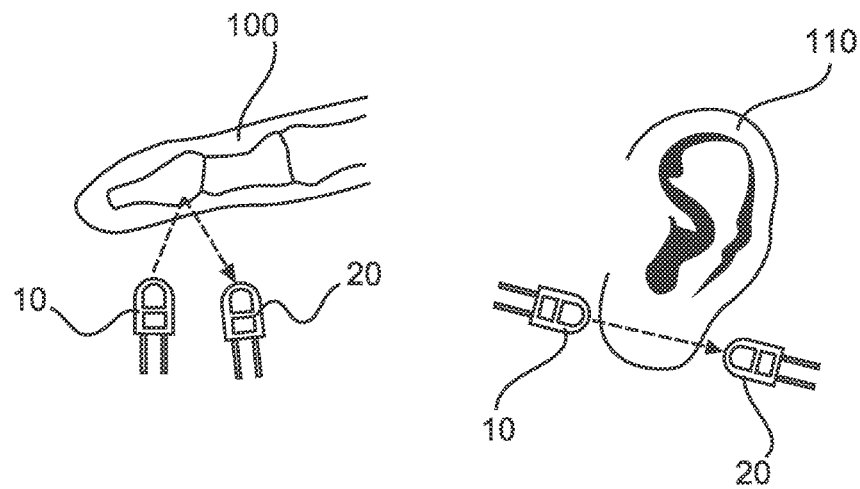
FIG. 1 shows two typical conventional implementation forms for PPG sensors.
Figure 2:
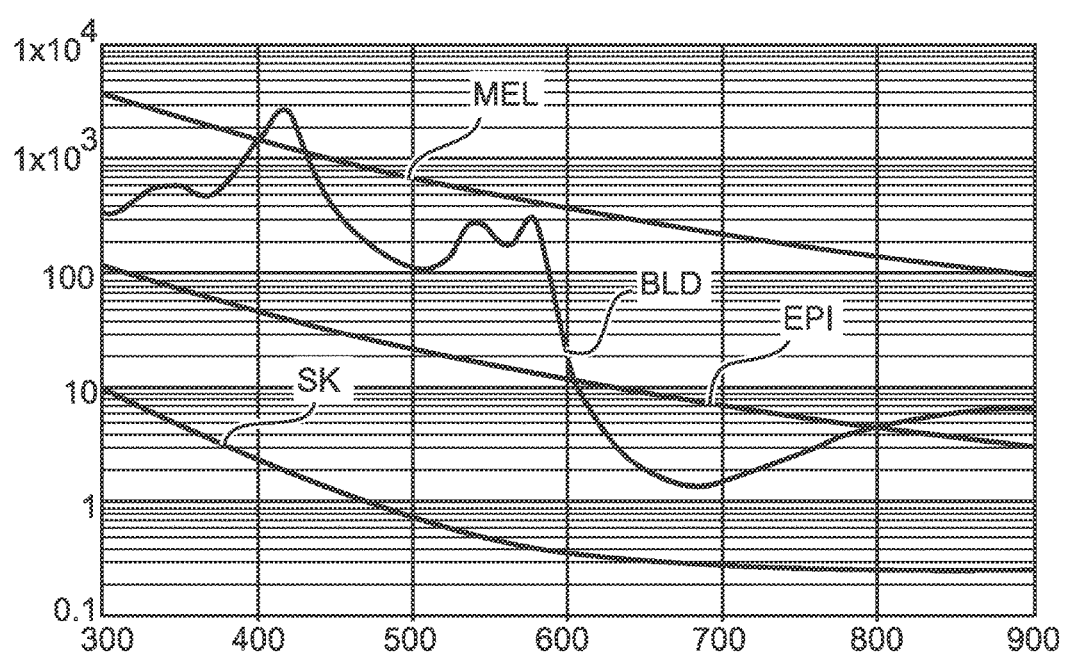
FIG. 2 shows a diagram indicating wavelength dependent absorption coefficients of various materials including blood and skin.

FIG. 2 shows a schematic diagram indicating wavelength-dependent characteristics (i.e., absorption curves) of absorption coefficients ($\mu$ [$cm^{-1}$]) of most relevant materials or matters within the ultraviolet, visible and infrared range. More specifically, the characteristics of skin (SK), whole blood (BD), melanosome (MEL), and epidermis (EPI), are shown. It is noted that the absorption curve of blood shown in FIG. 2 is based on a typical hemoglobin concentration of 150 gr Hb/l. The absorption curve of blood (BLD) comprises two interesting areas. These are the areas with a steep slope (i.e., high $d\mu/d\lambda$) in the optical blue and amber/red region of the spectrum of visible light. Of these, the latter range (~600 nm) has the highest slope, largest range, and more importantly, the absorption of light by the skin (SK) approaches its minimum slope and minimum value there. Therefore, choosing two very close wavelengths in this region will not pick-up any significant motion artefacts, while still providing a good PPG signal. More specifically, the diagram of FIG. 2 shows absorption spectra of different biological chromophores. Blood (BLD) is represented by the absorption spectrum of oxyhemoglobin ($HbO_2$), since for normal healthy people oxygen saturation is in the order of >90% and the influence of deoxyhemoglobin will therefore be minimal. From the diagram it is clear than for PPG sensors the major disturbance may result from melanin absorption. Because of the longer optical path length the absorption in skin is much higher than in blood, resulting in a large DC (LF) component in the order of 100 times the wanted PPG signal. This absorption is also the major cause of motion artefacts, because any change in optical path-length through the skin will be much larger than any PPG signal.

According to the first embodiment, the skin signal (and thereby a major cause of motion artefacts) can be removed or at least suppressed by providing two light sources which generate the above mentioned two wavelengths and which are driven out of phase, such that the detected PPG signal is modulated by a predetermined frequency f. Because the PPG signal has now been transferred to a higher frequency, it can be AC detected using e.g. a lock-in amplifier without interference by the otherwise cumbersome DC/LF disturbances.

A lock-in amplifier (also known as a phase-sensitive detector) is a type of amplifier that can extract a signal with a known carrier wave from an extremely noisy environment. In essence, a lock-in amplifier takes the input signal, multiplies it by a reference signal (either provided from the internal oscillator or an external source), and integrates it over a specified time, usually on the order of milliseconds to a few seconds. The resulting signal is a DC signal, where the contribution from any signal that is not at the same frequency as the reference signal is attenuated close to zero. The out-of-phase component of the signal that has the same frequency as the reference signal is also attenuated (because sine functions are orthogonal to the cosine functions of the same frequency), making a lock-in amplifier a phase-sensitive detector. It is essentially a homodyne detector followed by low pass filter that is often adjustable in cut off frequency and filter order. Lock-in amplifiers may use analog frequency mixers and RC filters for demodulation, or they may be implemented by fast digital signal processing for example on a filed-programmable gate array (FPGA).

An additional benefit of the solution according to the first embodiment is that the wanted signal is now strictly an AC signal and can thus be AC coupled to thereby remove any DC component. This provides a higher dynamic range and thus enables use of a much lower resolution of the ADC.

Therefore, the PPG sensor according to the first embodiments comprises two light-sources with different, but very close wavelengths, an oscillator for driving the two light sources out of phase and with the frequency f, one or more photo-detectors, and an AC-coupled amplifier.

The two light-sources with slightly different emission wavelengths can e.g. be implemented with two LEDs from the same type but from different colour bins. Alternatively, two equal LEDs each with a slightly different band-pass filter (BPF) can be used. The LEDs (or band-pass filters of both filters) are chosen such that their emission wavelengths have (as good as possible) equal scattering and absorption parameters in the tissue and are located in a steep part of the blood absorption curve of FIG. 2. E.g., in the amber/red region of the spectrum of visible light around 600 nm or in the blue region, where the slope of the absorption curve is very steep (note that a log scale in used in FIG. 2).

Figure 3:
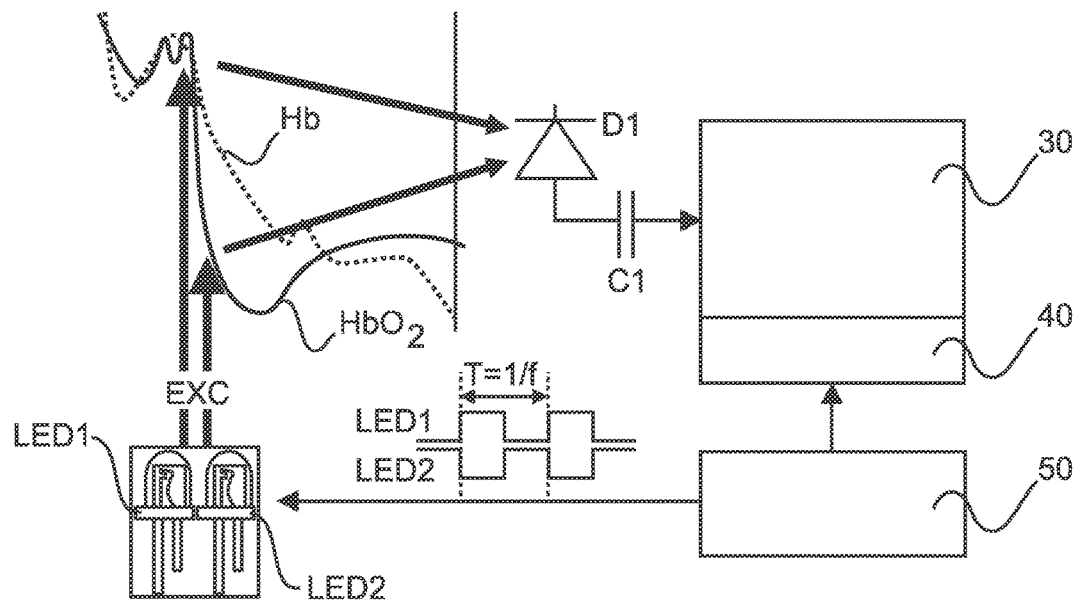
FIG. 3 shows an operating principle of a PPG sensor device according to a first embodiment.

FIG. 3 shows the principle of operation underlying the first embodiment. The two almost equal light sources LED1 and LED2 are driven out of phase and with a predetermined frequency f by a signal generated by an oscillator 50. The excitation light EXC emitted by the light sources LED1 and LED2 will lead to alternating samples at two different parts of the very steep blood absorption curve ($HbO_2$), so that a modulated AC-type of PPG signal is generated by a photo diode D1 at the optical receiver side. The obtained AC PPG signal can then be AC-coupled via a capacitor C1 to an electronic circuit 30 including an amplifier and an ADC, to thereby remove any DC part (including unwanted DC and LF components, such as ambient light) and provide a large dynamic range filled with the useful PPG signal component only. The useful PPG signal is then detected by a lock-in amplifier 40 which receives its reference signal from the oscillator 50.

Figure 4:
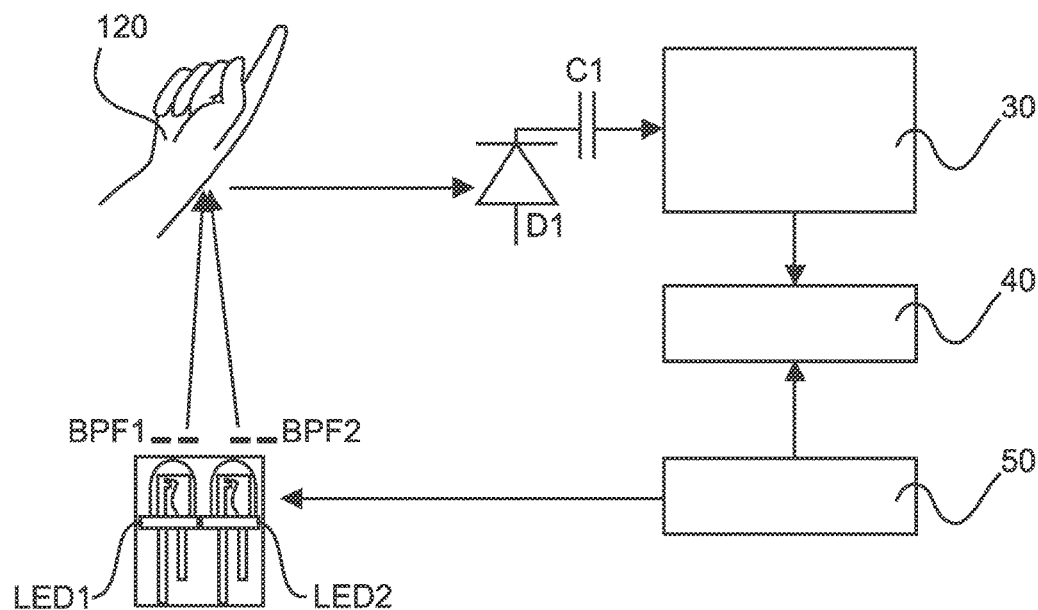
FIG. 4 shows a schematic block diagram of the PPG sensor device according to the first embodiment.

FIG. 4 shows a schematic block diagram of a PPG sensor device according to the first embodiment, where components with same designation or reference numerals have the same functionality as described in connection with FIG. 3. Both lights sources LED1 and LED2 are of the same wavelength range (e.g. amber light with a peak wavelength of 586 nm). The output light of the light sources LED1 and LED2 passes through respective band-pass filters BPF1 and BPF2 which may be standard of-the-shelf filters with e.g. characteristics 580×10 nm and 595×10 nm, i.e., center wavelengths of 580 nm and 595 nm, respectively, and bandwidths of 10 nm each. The intensities in both pass bands are equalized by adjusting the LED currents during production (fixed value setting). The frequency of the oscillator 50 is chosen such that a clear separation with the frequency of interference is achieved. As an example, frequencies above 100 Hz or above 1 kHz may be used.

Optionally, the two equal type light sources LED1 and LED2 can be replaced by two different light sources (which are of same type, but neighbouring colour bins approximately equal to the central wavelength of correspondingly replaced filters). The lock-in amplifier 40 can be implemented in firmware, but an analogue version may also be used.

According to a first modification of the first embodiment, the two light sources LED1 and LED2 may be replaced by light sources for emitting light in the blue wavelength region which is also suitable for generating the desired AC-type PPG signal.

According to a second modification of the first embodiment, the AC coupling by the capacitor C1 may be replaced with a DC restoration loop, e.g., a subtraction of a correction current at the input of the amplifier of the electronic circuit 30. A current source supplying this correction current may be controlled in a feedback loop in a manner so that the DC value at the amplifier input or output is at a suitable level (e.g. zero or any other suitable level).

It is to be noted that the intensities in both pass bands of the filters BPF1 and BPF2 should be at least close to equal to ensure that the rejection ratio of the motion artefacts will be maximum. In some embodiments these two intensities are chosen with a small difference such that they compensate the difference in absorption of the main interfering matter (melanin), i.e., the intensities should have the opposite slope of melanin in the chosen wavelength range. Alternatively, they can be chosen to have equal intensities. The intensities of the light sources LED1 and LED2 can be adjusted at production, but can also be regulated via a respective control loop. This provides the additional advantage that the PPG sensor may as well be used as a motion sensor measuring e.g. activity.

According to a third modification of the first embodiment, the PPG sensor device can be adapted to pick up selected motion artefacts by introducing an unbalance in both wavelength intensities. This unbalance can be modulated at a second frequency f2.

The third modification can be equal to any of the previous modifications of the first embodiment, but here the amplitude of one or both of the light sources LED1 and LED2 is modulated at the second (different) frequency f2. Thereby, two carrier frequencies are generated: one for the PPG signal and one for a combination of PPG signal and motion artefacts. Two digital (firmware) lock-in amplifiers are then used to synchronously detect both signals. Subtraction of the scaled PPG signal from the second signal will then result in a pure motion signal. This motion signal can then be used to monitor activity.

Figure 5:
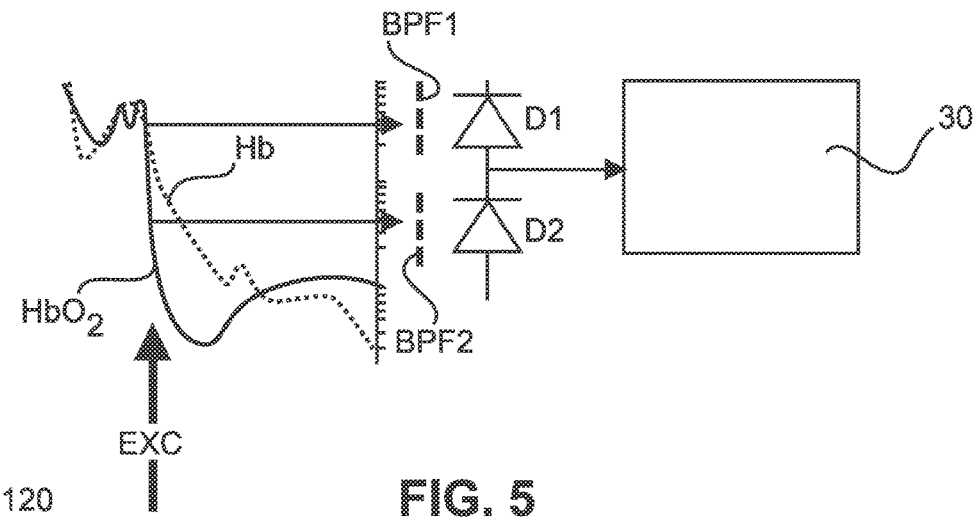
FIG. 5 an operating principle of a PPG sensor device according to a second embodiment.

FIG. 5 shows an operating principle of a PPG sensor device according to a second embodiment. Here, a PPG sensor structure is provided, that removes common mode signals, while outputting only the differential mode. Since PPG signals are normally not differential signals, additional measures are added to create such a differential signal. The PPG sensor device of the second embodiment comprises one or more light source(s) and two or more wavelength sensitive photo detectors.

According to FIG. 5, the PPG sensor device comprises two photo detectors each with slightly different wavelength sensitivity. They can e.g. be implemented with two band-pass filters BPF1 and BPF2 in front of two photo diodes D1 and D2. The pass bands of both filters BPF1 and BPF2 are selected such that wavelengths in both pass bands have equal or at least similar scattering and absorption parameters in the tissue. This ensures that this part of both detector inputs experiences equal scattering and absorption, so that at least a nearly perfect common mode (CM) signal is obtained. For skin, this can be achieved e.g. in the 500-1000 nm band (cf. "SK" curve in FIG. 2). Even in this very wide band the skin absorption does not change more than a factor of 3 to 4. The change in absorption for the epidermis (EPI) is larger, but still very much lower than that of blood (in e.g. a small band around 600 nm).

Furthermore, the pass bands of both filters BPF1 and BPF2 are selected so that they are located in a steep part of the blood absorption curve (cf. "BLD" curve in FIG. 2). E.g., at around 600 nm the slope of the absorption curve is very steep. A small difference between the two pass bands will then still provide more that an order of magnitude difference in absorption coefficients between the two wavelengths, thus creating the desired differential PPG signal.

Hence, the photo detector configuration shown in FIG. 5 will reject the common mode signal (because the two photo currents generated in the photo diodes D1 and D2 will be subtracted from each other), and the output of the amplifier in the electronic circuit 30 will only be the wanted differential PPG signal originating from blood.

Figure 6:
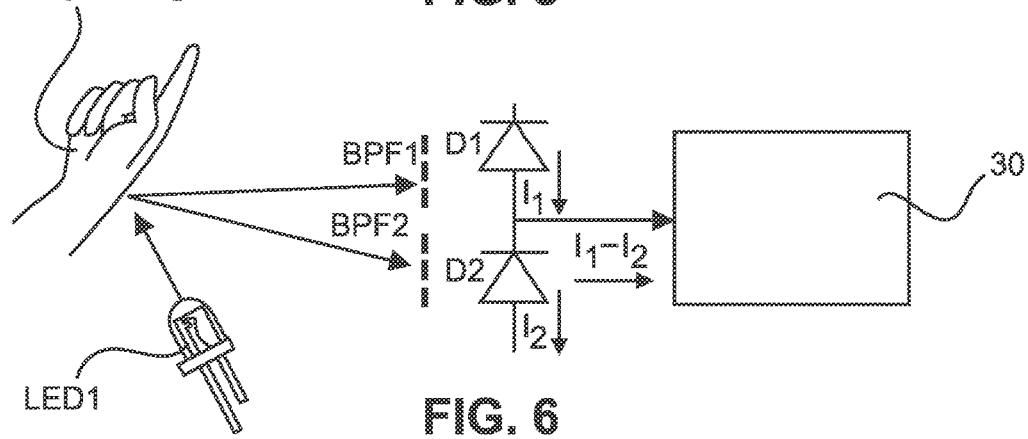
FIG. 6 shows a schematic block diagram of the PPG sensor device according to the second embodiment.

FIG. 6 shows a schematic block diagram of the PPG sensor device according to the second embodiment.

Nowadays, PPG sensors are not only medical devices, but also implemented in consumer products like sport-watches.

These require low part count, and low power consumption. It is therefore desirable to implement the PPG sensor using one light source only. This can be achieved by using the single light source LED1 (e.g., LED or other source with appropriate emission spectrum) of the second embodiment. The emission spectrum of the light source LED1 should be wide enough to include both chosen pass bands. This is easily accomplished because the spectral width of an LED is often wider than 20 to 30 nm (full width at half maximum (FWHM)). If the chosen pass bands are further apart a phosphor converted LED (e.g. white, lime or amber) can be used.

Figure 7:
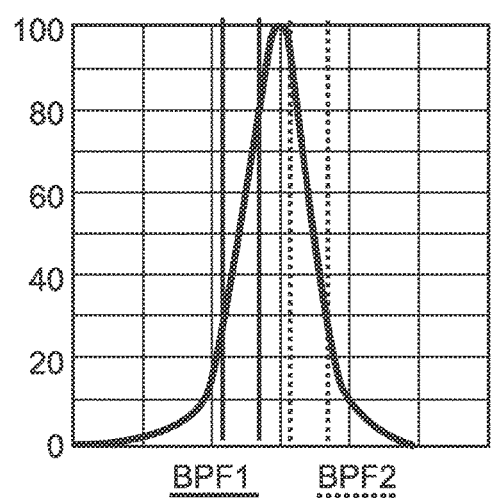
FIG. 7 shows an exemplary emission spectrum of a light emitting diode and filter characteristics of appropriate band-pass filters according to the second embodiment.

FIG. 7 shows an exemplary emission spectrum of a light emitting diode and filter characteristics of appropriate band-pass filters BPF1 and BPF2 according to the second embodiment. As can be gathered from FIG. 7, both 'colors' of light in the respective pass bands of the filters BPF1 and BPF2 are part of the LED spectrum. From this figure it is also clear that instead of two band pass filters, a short pass and long pass filter with equal or nearly equal cut-off wavelength can be used.

Hence, the wavelength separation between both pass bands is so little that light detected by the photo diodes D1 and D2 not originating from blood has experienced the same absorption and scattering. Therefore, the respective currents $I_1$ and $I_2$ generated by the photo diodes D1 and D2 for these parts of the light spectrum are equal and therefore suppressed by the subtraction action at the input of the amplifier of the electronic circuit 30. However, for blood the absorption in both pass bands differs considerable, and this is therefore a differential signal (in the sense that it has different intensities in both pass bands). This PPG signal component is attenuated a little by the subtraction action, but because of the difference between both is in the order of a magnitude this still results in a large PPG signal.

Figure 8:
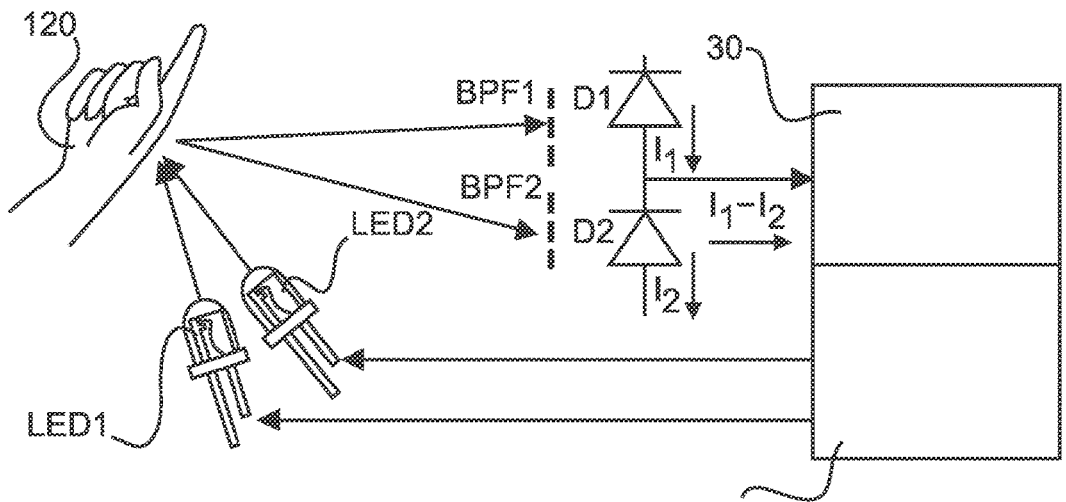
FIG. 8 shows a schematic block diagram of a PPG sensor device according to a third embodiment.

FIG. 8 shows a schematic block diagram of a PPG sensor device according to a third embodiment.

LED spectra have tolerances, so do the pass bands of the band-pass filters. At larger tolerances, the attenuation of the DC component of the PPG signal can become too low. If the costs of tighter tolerances become too high, the problem can be solved by using two light sources LED1 and LED2 with different emission wavelengths. For example, two light sources (e.g. LEDs) of the same type but with different color bins. By controlling the currents of the two light sources LED1 and LED2 via a feedback loop 60 for DC cancellation based on any remaining DC output of the amplifier of the electronic circuit 30, the balance can be restored, such that the attenuation of the unwanted DC or LF components is largest.

Figure 9:
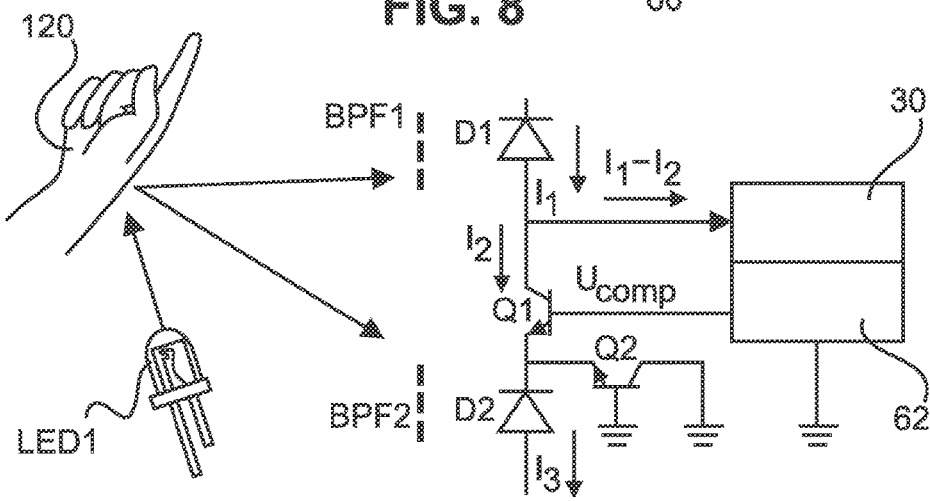
FIG. 9 shows a schematic block diagram of a PPG sensor device according to a fourth embodiment.

FIG. 9 shows a schematic block diagram of a PPG sensor device according to a fourth embodiment.

As already mentioned above, due to production tolerances in light sources (e.g. LEDs) and optical filters, the rejection of the common mode signal can become less than desired. This embodiment solves this problem via addition of a controllable current divider comprising transistors Q1 and Q2. It is assumed that the second one BPF2 out of the two band-pass filters BPF1 and BPF2 has a longer wavelength. This means that the current $I_3$ generated by the second photo diode D2 is always slightly larger than the current $I_1$ generated by the first photo diode D1, because the absorption of haemoglobin, skin and melanin all decrease with increasing wavelength at the large slope around 600 nm in $HbO_2$ absorption. It is noted that, if needed, this situation can be forced by providing a bigger second photo diode D2 or by slightly reducing the transmission in the pass band of first band-pass filter BPF1). The DC component (i.e. skin and melanin absorption) of this fractional higher photocurrent can be used to compensate for the production tolerances by shunting away a certain percentage of this current with the current divider. The ratio between dc collector currents of the transistors Q1 and Q2 is controlled by control voltage $U_{comp}$ according to:

$$\frac{I_{C,Q1}}{I_{C,Q2}} = e^{\left(\frac{U_{comp}}{V_T}\right)}$$

with $V_T$=kT/q≈26 mV

The control voltage $U_{comp}$ is generated by a DC cancellation feedback loop 62 based on a remaining DC component in the output signal of the amplifier of the electronic circuit 30.

For $U_{comp}$=0V, the ratio between the two collector currents of the transistors Q1 and Q2 can be set to 1, so that half of the photocurrent $I_3$ of the second photo diode D2 will be shunted to ground. The ratio is independent of the value of the current $I_3$ itself, so that the balance in the common mode component of both photo diode currents can be controlled with the control voltage $U_{comp}$. This can be done only once during production with a fixed voltage or continuously using the DC cancellation feedback loop 62 with a bandwidth such that PPG signals are not affected.

Because of the exponential relationship, the divider ratio will saturate for relative low control voltages. E.g., for $U_{comp}$=118.8 mV, the ratio will already reach 99% so that only 1% of the current $I_3$ will be shunted away. This high gain can be reduced by adding emitter degeneration resistors.

Figure 10:
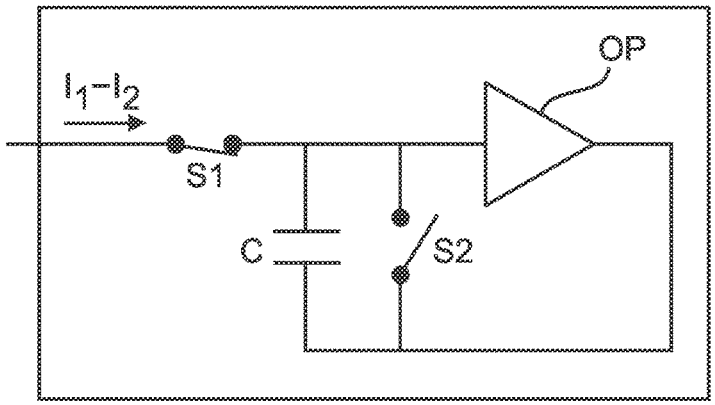
FIG. 10 shows a schematic circuit diagram of a switched integrator amplifier for use in the PPG sensor device according to the fourth embodiment.

FIG. 10 shows a schematic circuit diagram of a switched integrator amplifier for use in the PPG sensor device according to a first modification of the fourth embodiment. Here, a switched integrator amplifier is used as a current-to-voltage convertor in the electronic circuit 30. The switched integrator amplifier comprises first and second controlled switches S1 and S2 and an operational amplifier OP with an integrating feedback capacitor C switched by the second switch SW2.

After removing the common mode ('DC') component, the resulting photo current is mainly a PPG-only signal and is therefore a very small AC current. This allows for large amplification which can be achieved with superior signal-to-noise ratio (SNR) using switched integrating transimpedance amplifiers (instead of normal transresistance photo diode amplifiers). These SNR advantages can be advantageously exploited in various embodiments due to the DC removal.

Figure 11:
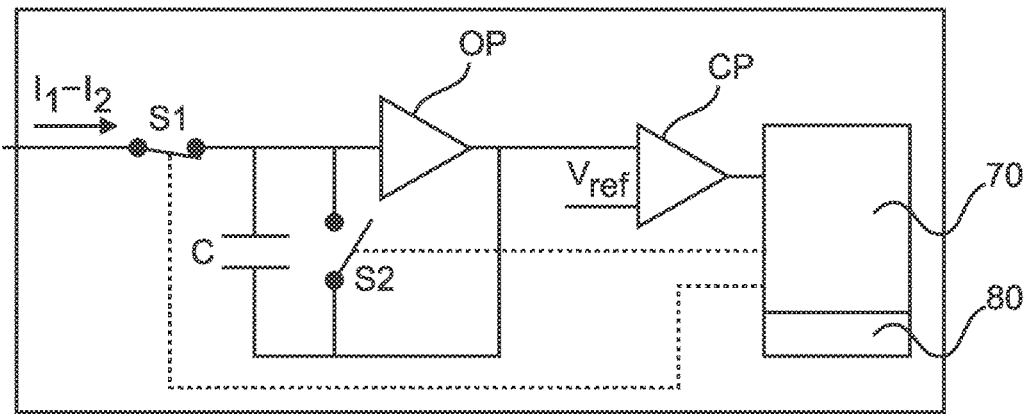
FIG. 11 shows a schematic circuit diagram of a current-to-time converter for use in the PPG sensor device according to the fourth embodiment.

FIG. 11 shows a schematic circuit diagram of a current-to-time converter for use in the PPG sensor device according to a second modification of the fourth embodiment.

The modified fourth embodiment of FIG. 10 can be enhanced by letting the switched integrator function as a current-to-time converter, thereby also replacing the conventional analogue-to-digital converter (ADC).

The switches S1 and S2 of the switched integrator amplifier are controlled by a micro controller 70 which also runs a timer 80. When the integration cycle starts, the timer 80 is also reset. The output voltage of the integrator increases linear with time (i.e. $(I_2-I_1) \cdot t/C$). The integration operation of the switched integrator amplifier part continues until the output voltage of the integrator reaches a predetermined reference voltage level $V_{ref}$ at which time a comparator CP interrupts the microcontroller 70 and the timer 80. The timer value is then related to the input current as $I(t)=V_{ref}*C/t$. Therefore, the PPG signal can be measured by counting the duration of the integration cycle. Since absolute accuracies are not important, accurate values of the capacitor C and the reference voltage level $V_{ref}$ are not needed as long as sufficient short-term stability is guaranteed. Since most modern microcontroller are equipped with a counter or timer and with a comparator, this modification of the fourth embodiment saves the cost of an ADC which is normally needed in a conventional PPG sensor.

According to a third modification of the fourth embodiment, the two band-pass filters BPF1 and BPF2 are replaced with one dichroic beam splitter which is an optical device with a dichroic optical coating that splits a beam of light in two beams. Depending on its characteristics, the ratio of reflection to transmission will vary as a function of the wavelength of the incident light. In this case ambient light is not rejected. Therefore, the PPG sensor should be shielded, or the light source(s) could be modulated in combination with lock-in amplifier as described in connection with the first embodiment.

Figure 12:
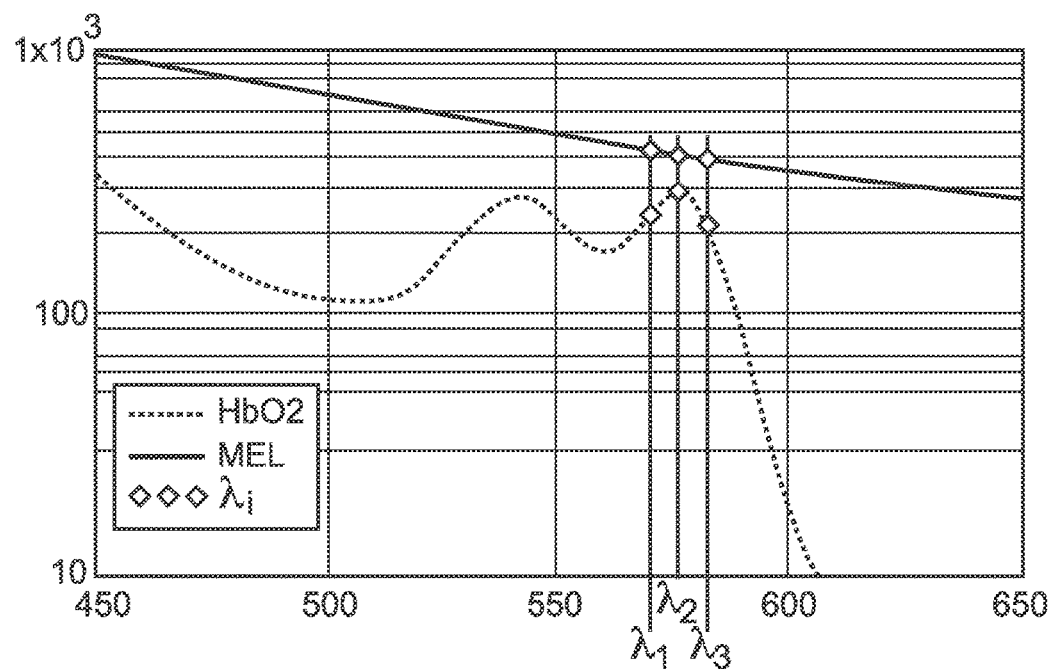
FIG. 12 shows a diagram indicating wavelength-dependent absorption coefficients of blood and tissue and values of closely separated wavelengths for use in a fifth embodiment.

FIG. 12 shows a diagram indicating wavelength-dependent absorption coefficients of blood and tissue and values of closely separated wavelengths for use in a fifth embodiment.

The close-up of FIG. 12 indicates the absorption spectra of two most important contributors in PPG sensing, namely oxyhemoglobin ($HbO_2$) and skin tissue (MEL) with a certain melanin concentration (here a light coloured skin is shown for illustrative purposes, but for a darker skin the absorption can be >100 times larger). Also indicated are values at three closely separated wavelength ($\lambda_1<\lambda_2<\lambda_3$).

The three wavelengths $\lambda_1$, $\lambda_2$ and $\lambda_3$ are chosen such that the tissue absorption at $\lambda_2$ equals the average of the other two tissue absorptions (i.e. $[\mu_{a\_tissue}(\lambda_1)+\mu_{a\_tissue}(\lambda_3)]/2=\mu_{a\_tissue}(\lambda_2)$), while this is certainly not the case for the blood absorption. Subtracting the average of the $\lambda_1$ and $\lambda_3$ measurements from the $\lambda_2$ measurement will now totally reject the influence of skin absorption. And since $[\mu_{a\_blood}(\lambda_1)+\mu_{a\_blood}(\lambda_3)]/2 \neq \mu_{a\_blood}(\lambda_2)$, the PPG signal will not be rejected by the subtraction at two photo diodes D1 and D2 at the receiving end.

Although this example is shown for a particular wavelength (e.g. 576±6 nm), it is clear that the relevant spectra show more possibilities (e.g. around 560 nm, 541 nm, etc). It is important (but not mandatory) to choose the three wavelengths close together because the proposed approach does not take into account the wavelength dependencies of other optical parameters of the skin, e.g., scattering, anisotropy and refractive index. These parameters will also change with wavelength, so that choosing the wavelength further apart will lead to different optical paths being sampled and compared and therefore to a lower rejection of unwanted DC or LF components (e.g. motion artefacts).

Choosing the three wavelengths close together provides the additional advantage that they can be produced from a single source (e.g. a normal LED easily has a FWHM of 20 to 30 nm making it an ideal source for this fifth embodiment). A further advantage is less deviation in detector sensitivity if the wavelengths are nearly equal.

Figure 13:
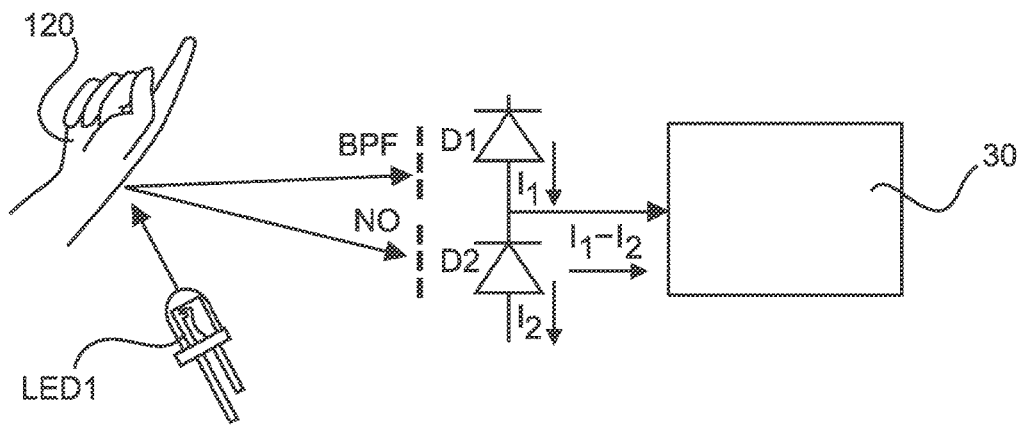
FIG. 13 shows a schematic block diagram of a PPG sensor device according to a fifth embodiment.

FIG. 13 shows a schematic block diagram of a PPG sensor device according to the fifth embodiment.

The PPG sensor device of the fifth embodiment is constructed using one light source LED1 and two photo detectors each with different wavelength sensitivity. They can e.g. be implemented with two different filters in front of two photo diodes D1 and D2. The first detector is equipped with a band-pass filter BPF and the second detector is equipped with a notch filter NO with an opposite band-reject (notch) characteristic. Thus, the band-pass filtered first detector will measure signal components within the central wavelength region ($\lambda_2$), while the second detector equipped with the notch filter will measure the sum of signal components within the outer wavelength regions ($\lambda_1$ and $\lambda_3$).

The photo-detector configuration of the fifth embodiment will reject the common mode signal, because the two photo currents $I_1$ and $I_2$ will be subtracted from each other at the input of the electronic circuit 30, and the output of the electronic circuit 30 will only be the wanted differential PPG signal originating from blood. Therefore, the amplifier of the electronic circuit 30 only needs to amplify the PPG signal, freeing up valuable dynamic range for amplifier and ADC.

Figure 14:
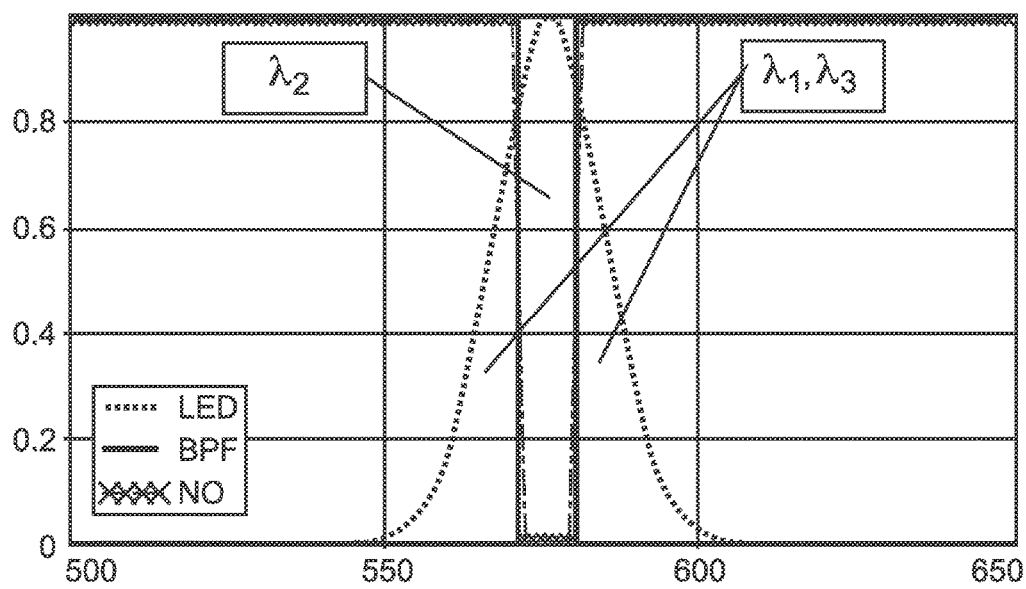
FIG. 14 shows filter characteristics of a band-pass filter and a notch filter used in the fifth embodiment.

FIG. 14 shows filter characteristics of the band-pass filter BPF and the notch filter NO used in the fifth embodiment.

The outer boundaries of the pass band of the notch filter NO will be formed by the spectral limitation of the light source LED. Alternative, the second filter can have a double band-pass design, which eliminates the source bandwidth requirements.

Furthermore, the size of the detectors can be scaled such that the measured tissue absorption in the first photo diode D1 ($\lambda_2$) and in the second photo diode D2 ($\lambda_1+\lambda_3$) are equal. Generally, this is the case if the first photo diode D1 is twice as large as the second photo diode D2.

To ensure that both signals come from the same optical path, it is important that the two detectors are placed physically as close together as possible. This can be achieved optically by using a beam splitter. An alternative is a symmetrical positioning around the source.

Furthermore, the PPG sensor device of the fifth embodiment can also be implemented with three detectors (e.g., the second photo diode D2 is implemented as two separate photo diodes) and one band-pass filter (for the first photo diode D1) or three separate band-pass filters for each photo diode.

To summarize, a method and apparatus have been described for measuring a tissue variation signal (e.g. PPG signal) without large DC or LF offset which normally limit the sensor accuracy through motion artefacts and/or dynamic range requirements. The proposed solution is based on a separation of the PPG signal from the disturbance. This can be achieved by creation of a modulated PPG signal, or by creation of a differential PPG signal and an optimized sensor configuration which is adapted to remove DC or LF components. The common basis of the embodiments is the spectral difference between blood and other motion sources (e.g., skin, melanin, etc.). Either a large slope difference is used directly for creating common mode (CM) and differential mode (DM) signals or modulating signal and interference with different gains, or different parts of the spectrum with different changes in absorption coefficients are used to also create CM/DM signals. As regards the specific absorption coefficients, a substantial difference can be understood in a sense that the difference between respective absorption coefficients should be greater than 50 $cm^{-1}$ while the difference between the first and second wavelengths should be not be greater than 30 nm, or, in some embodiments, not greater than 20 nm. This difference covers the use of the large blue slope, the amber/red slope and the smaller slopes in-between of the absorption curve of blood.

While various embodiments have been illustrated and described in detail in the drawings and foregoing description, such illustration and description are to be considered illustrative or exemplary and not restrictive. The scope of the present disclosure is not limited to the disclosed embodiments. E.g., although the above first to fifth embodiments and their modifications have been described in connection with a transmissive type of PPG sensor, they all can be implemented for a reflective type of PPG sensor as well.

Furthermore, the proposed measurement concepts of the first to fifth embodiments can be applied to other optical sensors which are influenced by different absorption characteristics of different materials.

Other variations to the disclosed embodiments can be understood and effected by those skilled in the art in practicing the methods and principles disclosed herein, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

The foregoing description details certain embodiments. It will be appreciated, however, that no matter how detailed the foregoing appears in text, the principles described herein may be practiced in many ways, and is therefore not limited to the embodiments disclosed. It should be noted that the use of particular terminology when describing certain features or aspects of the embodiments should not be taken to imply that the terminology is being re-defined herein to be restricted to include any specific characteristics of the features or aspects of the embodiments with which that terminology is associated.

A single unit or device may fulfill the functions of several items recited in the claims. The mere fact that certain measures are recited in mutually different dependent claims does not indicate that a combination of these measures cannot be used to advantage.

The invention claimed is:

1. An apparatus for optical sensing of a variation of a matter provided in a tissue region, the apparatus comprising:
   at least one optical radiation source for transmitting a first optical signal of a first wavelength and a second optical signal of a second wavelength towards a tissue region, wherein a change of the matter's wavelength-dependent absorption coefficient between the first wavelength and the second wavelength differs by more than 50 cm-1 from a corresponding change of the wavelength-dependent absorption coefficient of other matter which influences the first and second optical signals during transmission, while the difference between the first and second wavelengths is not greater than 30 nm;
   at least one optical radiation detector for detecting a first portion of the first optical signal reflected at or transmitted through the tissue region and a second portion of the second optical signal reflected at or transmitted though the tissue region; and
   at least one filter for filtering a predetermined component of the first portion of the first optical signal and a predetermined component of the second optical signal so that an unwanted component caused by the other matter is suppressed before amplification and subsequent signal processing.

2. The apparatus of claim 1, wherein the at least one optical radiation source is adapted to generate the first and second wavelengths with a separation of less than 20 nm.

3. The apparatus of claim 1, further comprising a modulator for modulating the amplitudes of the first and second optical signals out of phase at a predetermined frequency, and wherein the at least one filter comprises a capacitor or a DC restoration loop for removing a DC component as the unwanted component of the first and second portions.

4. The apparatus of claim 3, wherein the modulator is adapted to modulate the first and second optical signals to be alternately switched on and off at the predetermined frequency.

5. The apparatus of claim 3, further comprising a further modulator for modulating the amplitudes of the first and second optical signals by a further predetermined frequency which differs from the predetermined frequency, to thereby introduce an unbalance of intensities of the first and second optical signals so as to obtain a motion component in the first and second portions.

6. The apparatus of claim 3 wherein the modulator is adapted to modulate the unwanted component of the first and second portions.

7. The apparatus of claim 3, wherein the modulator is adapted to modify the first and second optical signals at a second frequency that is different from the predetermined frequency such that a first carrier frequency is generated for the PPG signal and a second carrier frequency is generated for a combination of the PPG signal and motion artefacts.

8. The apparatus of claim 1, wherein the at least one filter comprises a first band-pass filter for filtering the first wavelength and for supplying the filtered output signal to a first optical radiation detector of the at least one optical radiation detector, and a second band-pass filter for filtering the second wavelength and for supplying the filtered output signal to a second optical radiation detector of the at least one optical radiation detector, and wherein the apparatus is adapted to subtract electrical output signals generated by the first and second optical radiation detectors from each other.

9. The apparatus of claim 1, wherein the at least one optical radiation source is adapted to generate a third optical signal of a third wavelength, wherein the first, second and third optical wavelengths are selected so that the value of the wavelength-dependent absorption of the other matter at the second wavelength equals the average of the values of the wavelength-dependent absorption of the other matter at the first and third wavelengths, wherein the at least one filter comprises a first filter for filtering the second wavelength only and for supplying the filtered output signal to a first optical radiation detector of the at least one optical radiation detector and a second filter for filtering the first and third wavelengths only and for supplying the filtered output signal to a second optical radiation detector of the at least one optical radiation detector, and wherein the apparatus is adapted to subtract electrical output signals generated by the first and second optical radiation detectors from each other to suppress the unwanted component.

10. The apparatus of claim 9, wherein the at least one optical radiation source comprises a first optical radiation source for generating the first optical signal and a second optical radiation source for generating the second optical signal, and wherein the apparatus further comprises a feedback loop for controlling the first and second optical radiation sources in response to a detected remaining amount of the unwanted component.

11. The apparatus of claim 8, further comprising a controllable current divider for adjusting the ratio of the electrical output signals of the first and second optical radiation detectors based on a control signal generated by a feedback loop in response to a detected remaining amount of the unwanted component.

12. The apparatus of claim 8, further comprising a switched integrator amplifier for amplifying the resultant signal of the subtracted electrical output signals.

13. The apparatus of claim 12, wherein the switched integrator amplifier is provided in a current-to-time converter circuit.

14. The apparatus of claim 12, wherein the first and second optical radiation detectors are scaled by size and or sensitivity.

15. The apparatus of claim 1, wherein the matter is blood and the other matter is skin tissue.

16. The apparatus of claim 1 wherein the first and second wavelengths are selected from an amber or blue wavelength region.

17. A method of optical sensing of a variation of a matter provided in a tissue region, the method comprising:
- transmitting by at least one optical radiation source a first optical signal of a first wavelength and a second optical signal of a second wavelength towards a tissue region, wherein a change of the matter's wavelength-dependent absorption coefficient between the first wavelength and the second wavelength differs by more than 50 cm-1 from a corresponding change of the wavelength-dependent absorption coefficient of other matter which influences the first and second optical signals during transmission, while the difference between the first and second wavelengths is not greater than 30 nm;
- detecting by at least one optical radiation detector a first portion of the first optical signal reflected at or transmitted though the tissue region and a second portion of the second optical signal reflected at or transmitted though the tissue region; and
- filtering by at least one filter a predetermined component of the first portion of the first optical signal and a predetermined component of the second optical signal so that unwanted components caused by the other matter are suppressed before amplification and subsequent signal processing.

18. The method of claim 17 wherein the first and second wavelengths are selected from an amber or blue wavelength region.

* * * * *